United States Patent [19]

Turner et al.

[11] 4,114,617

[45] Sep. 19, 1978

[54] APPARATUS FOR INFUSION OF A MEASURED VOLUME OF BLOOD

[76] Inventors: Thomas D. Turner, 1120 Warm Springs Ave., Boise, Id. 83702; Alan R. Benson, 3465 Minuteman Way, Boise, Id. 83706

[21] Appl. No.: 772,686

[22] Filed: Feb. 28, 1977

[51] Int. Cl.² .............................................. A61M 5/14
[52] U.S. Cl. .............................. 128/214 R; 128/214 F
[58] Field of Search .......... 128/214 R, 214 B, 214 F, 128/214.2, 234, 227, DIG. 12, 247, 273, 274

[56] References Cited

U.S. PATENT DOCUMENTS

| 1,282,000 | 10/1918 | Quayle | 128/214 R |
|---|---|---|---|
| 2,907,325 | 10/1959 | Burke | 128/214 C |
| 2,999,499 | 9/1961 | Willet | 128/214 R |
| 3,559,644 | 2/1971 | Stoft et al. | 128/214 F |
| 3,650,093 | 3/1972 | Rosenberg | 128/214.2 X |
| 3,886,937 | 6/1975 | Bobo et al. | 128/214 R |
| 4,030,495 | 6/1977 | Virag | 128/214 F |

*Primary Examiner*—Dalton L. Truluck
*Attorney, Agent, or Firm*—Paul F. Horton

[57] ABSTRACT

Apparatus is disclosed for the infusion of a measured volume of blood while simultaneously infusing other intravenous solutions. The infusion apparatus includes a first check valve connected to a blood container; a first Y-connector connected at one inlet to the first check valve and at the other inlet to a calibrated syringe with plunger, and at its outlet to a force operative check valve; a second Y-connector connected at one inlet to the distal end of the force operative check valve, at the other inlet to a second check valve connected to an intravenous solution container, and at its outlet is adapted to connect with a needle. A measured quantity of blood is withdrawn from the blood container into the calibrated syringe and is infused into the vein without disturbing the infusion of the I-V solution, and without manual manipulation.

5 Claims, 3 Drawing Figures

APPARATUS FOR INFUSION OF A MEASURED VOLUME OF BLOOD

BACKGROUND OF THE INVENTION

1. Field of the Invention

This invention relates in general to the administration of parenteral fluids and more particularly to the administration of measured quantities of blood during simultaneous infusion of other intravenous fluids.

2. Description of the Prior Art

During surgery it is often desirable to infuse blood while at the same time administering other essential fluids. It is also desirable, and frequently critical when operating on children, that accurately measured amounts of blood be infused to replace blood lost through the surgery. Time lost through manual manipulation of valves can have disastrous consequences. One standard procedure at the present time includes the use of a Y-connector wherein one inlet is connected to a manually operated valve attached to a blood bag, the other inlet is connected to a syringe, and the outlet is connected to a needle. The valve is opened, blood withdrawn into the syringe, the valve closed, and the blood infused. Disadvantages include possible blood withdrawal from the infant and the crucial time lost in manually operating the valve. A second procedure currently in use is the employment of a 3-way stopcock, one inlet being connected to the blood bag, the other inlet to a syringe, and the outlet to the needle. Proper manipulation of the stopcock prevents blood withdrawal from the infant but has the disadvantage of manual operation and separation of connectors too frequently occurs.

Relevant prior art includes the flexible check valve of Willet, U.S. Pat. No. 2,999,499, the administration apparatus of Moore, U.S. Pat. No. 2,866,457, and the more recent apparatus of Dabney, U.S. Pat. No. 3,844,283.

The system developed by Willet permits withdrawal of fluid from container 6 by retracting plunger 30 of syringe 26 while simultaneously flexing valve 22, the fluid then being injectible through needle 19 by placing a positive pressure on the plunger. While this procedure does away with stopcocks and the accidental discoupling of connectors therefrom, it has the disadvantage of allowing possible aspiration of air or body fluids through needle 19.

The apparatus of Moore does not permit aspiration of fluid from container 6 for aseptic infusion through needle 19. Dabney discloses apparatus for infusion of measured volumes of fluid but uses manually operated valves, has no provision for simultaneous infusion of other fluids, and is not a closed system and therefore unsuitable for administration of blood.

SUMMARY OF THE INVENTION

The present invention comprises apparatus for infusing measured volumes of blood while providing means for simultaneous infusion of other solutions. The apparatus includes a completely automatic valve system for withdrawing accurately measured volumes of blood from a container and infusing the blood so withdrawn into the recipient.

It is an object of the present invention, therefore, to provide an infusion system having an automatic valve system.

It is a further object of the present invention to provide an infusion system having automatic valves, wherein a calibrated volume of fluid may be withdrawn from a container and dispensed.

A further object of the present invention is to provide a closed, air-free system having a calibrated measuring chamber from which blood is directly received from a container and from which blood is directly infused into a recipient.

More particularly, it is an object of the present invention to provide an infusion system having a check valve to prevent backward flow into a container from which fluid is withdrawn; a force operative check valve preventing accidental gravitational infusion; and a second check valve preventing backflow into a second container from which a second fluid is being infused.

Additional objects and advantages will become apparent and a more thorough and comprehesive understanding may be had from the following description taken in conjunction with the accompanying drawings forming a part of this specification.

DETAILED DESCRIPTION OF THE INVENTION

Figure 1:
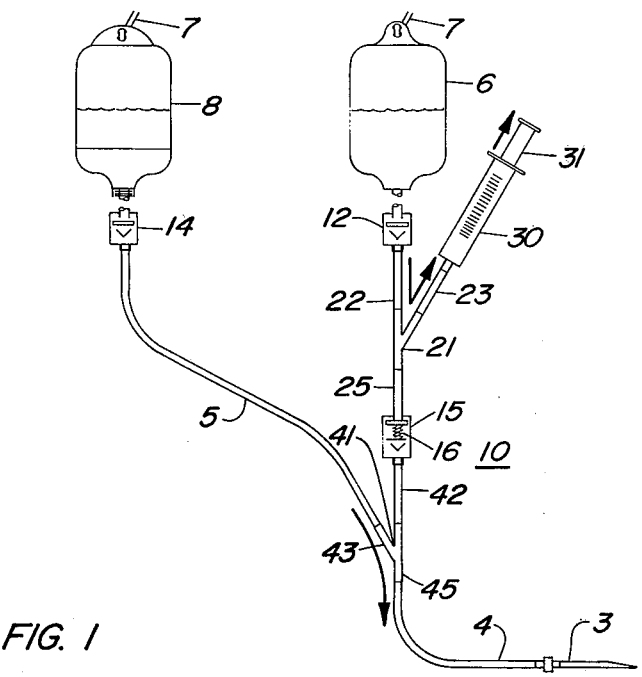
FIG. 1 is a schematic view of the apparatus of the present invention, showing withdrawal of blood into the syringe during simultaneous infusion of a second liquid.

Referring now to FIG. 1, a typical embodiment of infusion apparatus 10 of the present invention, as connected to a first solution container 6, hereinafter referred to as a blood container, and a second solution container 8, hereinafter referred to as an intravenous solution container, is disclosed. Infusion apparatus 10 includes first check valve 12, syringe 30 with plunger 31, first Y-connector 21, force operative check valve 15 and second Y-connector 41.

First check valve 12 is connected at its proximal end to the outlet of blood container 6, which is normally suspended from a hanger, designated generally by the numeral 7. Valve 12 is connected at its distal end to inlet leg 22 of Y-connector 21, either directly or by conduit extensions thereof. Connected to the other inlet leg, leg 23, is calibrated syringe 30 with its plunger 31. It is preferred that syringe 30 be connected to leg 23 by means of a conventional Luer-lock adapter, not shown, so that the syringe may be conveniently disconnected for ridding the system of air. Connected to outlet leg 25 of Y-connector 21 is the proximal end of force operative check valve 15. Valve 15 is connected at its distal end to inlet leg 42 of second Y-connector 41.

Second check valve 14 is connected at its proximal end to the outlet of intravenous solution container 8, suspended from hanger 7. Valve 14 is connected directly or by means of conduit 5 to the second inlet leg, leg 43, of second Y-connector 41. Outlet leg 45 of connector 41 is attached by means of conduit 4 to infusion needle 3, which is inserted into the recipient, intravenously.

First check valve 12 and second check valve 14 may be any of the check valves well known in the art such as ball valves or flap valves, it only being necessary that backflow into the containers not be permitted. Force operative check valve 15 may be of the conventional swing type or spring loaded type shown. It is essential that valve 15 be force operative, that is the valve must be in a normally closed position and opened only under pressure, the exact pressure being determined by the situation. It is essential that the blood from container 6 not be infused by gravity alone, but through the positive pressure applied by plunger 31 in syringe 30.

Figure 3:
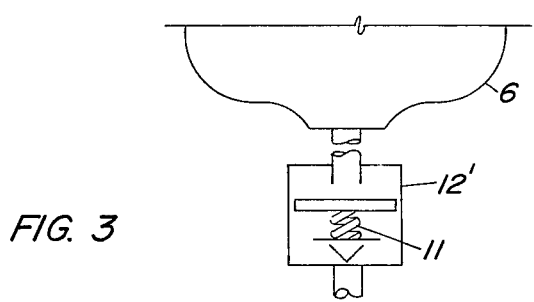
FIG. 3 shows an alternate embodiment of the present invention wherein a force operative check valve is substituted for a conventional check valve.

In one preferred embodiment of the invention, a force operative check valve 12', seen to advantage in FIG. 3, is substituted for the standard check valve 12. Force operative check valve 12' is identical in construction to force operative check valve 15. When blood container 6 is suspended above syringe 30, a pressure will be applied on plunger 31 of the syringe, tending to force the plunger out of the syringe, in instances where valve 12 is used. Many syringes frictionally engage the side walls of the syringe by means of rubber or plastic rings and the friction is sufficient so as not to be overcome by the pressure and the plunger is not moved. Sometimes however, there is no such frictional engagement, as where all glass syringes and plungers are use, and in such instances, valve 12' must be used.

Y-connectors 21 and 41 are identical in construction and include two inlet legs 22 and 23, and 42 and 43, respectively, and one outlet leg, 25 and 45, respectively. The term "Y-connector" as used in these specifications and in the appended claims refers to any connector having two inlet portals and one outlet portal, it being obvious that a T-connector would serve the same purpose. It is also to be noted that the term Y-connector also includes conduit extensions of the inlet and outlet portals and that the term "connected" as used in these specifications and in the appended claims means either a direct connection or a connection through a conduit. It is preferred that all conduits, valves, connectors, and the syringe and plunger be made of transparent material such as polyethylene, polyvinyl or glass so that the various solutions may be easily seen and so that any air may be removed from the system.

In operation, and after all air has been completely removed, the following procedure is employed. Plunger 31 is retracted in syringe 30, as shown in FIG. 1. Retraction of plunger 31 withdraws blood from container 6 through check valve 12 or 12'. Valve 12 is in the normally open position. When valve 12' is used, the retraction of the plunger causes forceful opening of the valve in overcoming the tension of spring 11 located therein, as shown in FIG. 3. Blood is thereby withdrawn from container 6 and into the calibrated syringe until a desired volume of blood has been obtained. Referring again to FIG. 1, it will be seen that the negative pressure applied to force valve 15, by retraction of the plunger, keeps that valve in a closed position. It will also be seen that the intravenous flow of solution from container 8, fed by gravity, is unaffected, as shown by the arrow.

Figure 2:
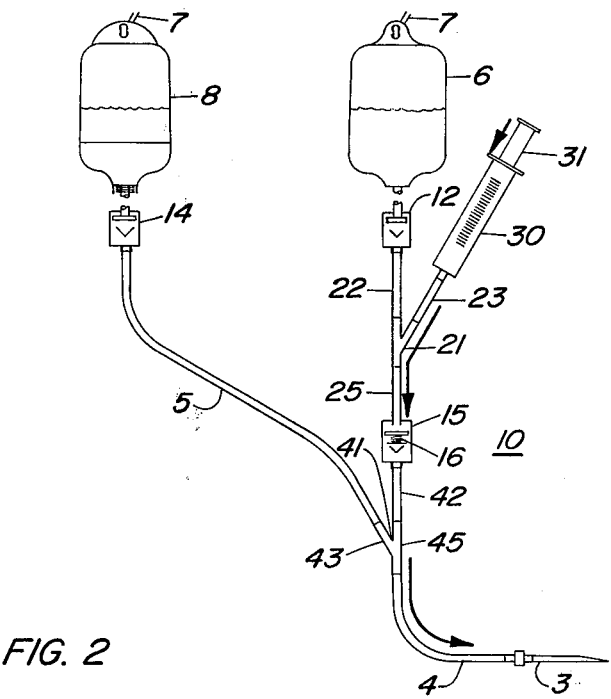
FIG. 2 shows the apparatus of FIG. 1 during infusion of the blood.

Once the syringe is filled to a desired capacity with blood, the system is ready for infusion to occur. The infusion process of the blood is shown in FIG. 2. As plunger 31 is pressed into syringe 30, the blood is forced through inlet 23 and outlet 25 of first Y-connector 21, through force operative check valve 15, into second Y-connector 41, through conduit 4, through needle 3, and into the vein. It will be seen that the positive pressure in first Y-connector 21, caused by pressing plunger 31 into syringe 30, causes closure of check valve 12 or 12' and opening of valve 15 by overcoming the resistance of spring 16 of force operative valve 15. Second check valve 14 will close if, on occasion, the pressure in conduit 5 exceeds the pressure in the distal port of valve 14, thereby keeping intravenous fluid contained in container 8 free from contamination. Otherwise, the solution from container 8 continues to flow.

Having thus described in detail, preferred embodiments of the present invention, it is to be appreciated and will be apparent to those skilled in the art that many physical changes could be made in the apparatus without altering the inventive concepts and principles embodied therein. The present embodiments are therefore to be considered in all respects as illustrative and not restrictive, the scope of the invention being indicated by the appended claims rather than by the foregoing description, and all changes which come within the meaning and range of equivalency of the claims are therefore to be embraced therein.

We claim:

1. In a system for administering two parenteral fluids including a first solution container and a second fluid container, apparatus for dispensing accurately measured amounts of solution from the first container, comprising:
   a first check valve connected at its proximal end to the first solution container;
   a calibrated syringe and plunger;
   a first Y-connector having a first and second inlet conduit and a common outlet conduit, said first inlet conduit connected to the distal end of said first check valve, said second inlet conduit connected to said syringe;
   a force operative check valve connected at its proximal end to said common outlet conduit of said first Y-connector;
   a second check valve connected at its proximal end to the second fluid container;
   a second Y-connector having a first and second inlet conduit and a common outlet conduit, said first inlet conduit connected to the distal end of said force operative check valve, said second inlet conduit connected to the distal end of said second check valve and said common outlet adapted to communicate with a needle.

2. The device as recited in claim 1, wherein said first check valve is a force operative check valve.

3. The device as recited in claim 2, wherein said first check valve includes a force operated compression spring for maintaining the valve in a closed position until force activated.

4. The device as recited in claim 1, wherein said first check valve, said first and second Y-connectors, said force operative check valve, said second check valve and all conduit extensions have transparent external side walls 5. In a system for administering at least two parenteral fluids including a first solution container and a second solution container, apparatus for dispensing accurately measured amounts of solution from the first container, comprising:
   a first check valve connected at its proximal end to the first solution container, said first check valve including a force operated compression spring for maintaining the valve in a closed position until force activated;
   a calibrated syringe and a plunger operable within said syringe for forcing a measured amount of blood to or from said syringe;

a first Y-connector having a first and second inlet conduit and a common outlet conduit, said first inlet conduit connected to the distal end of said first check valve, said second inlet conduit connected to said syringe;

a force operative check valve connected at its proximal end to said common outlet conduit of said first Y-connector, said force operative check valve including a force operated compression spring for maintaining the valve in a closed position until force activated;

a second check valve connected at its proximal end to the second solution container;

a second Y-connector having a first and second inlet conduit and a common outlet conduit, said first inlet conduit connected to the distal end of said force operative check valve, said second inlet conduit connected to the distal end of said second check valve and said common oulet adapted to communicate with a needle.

* * * * *